United States Patent [19]
Soldato

[11] Patent Number: 5,700,947
[45] Date of Patent: Dec. 23, 1997

[54] NITRIC ESTERS HAVING ANTI-INFLAMMATORY AND/OR ANALGESIC ACTIVITY AND PROCESS FOR THEIR PREPARATION

[75] Inventor: Piero Del Soldato, Monza, Italy

[73] Assignee: NICOX S.A., Paris, France

[21] Appl. No.: 624,508

[22] PCT Filed: Sep. 23, 1994

[86] PCT No.: PCT/EP94/03182

§ 371 Date: Apr. 5, 1996

§ 102(e) Date: Apr. 5, 1996

[87] PCT Pub. No.: WO95/09831

PCT Pub. Date: Apr. 13, 1995

[30] Foreign Application Priority Data

Oct. 6, 1993 [GB] United Kingdom ............ 9320599
May 10, 1994 [IT] Italy .................... MI94A0916

[51] Int. Cl.$^6$ .................................. C07D 209/04
[52] U.S. Cl. .................. 548/491; 548/576; 558/482; 558/483
[58] Field of Search .................. 548/491, 516; 558/482, 486

[56] References Cited

U.S. PATENT DOCUMENTS 3,758,544  9/1973  Alvarez ................... 260/465
5,049,694  9/1991  Bron et al. ............... 558/480

FOREIGN PATENT DOCUMENTS 1793828  4/1976  Germany.
2814556  10/1978  Germany.
1443429  10/1989  Germany.
9404484  3/1994  WIPO.
9412463  6/1994  WIPO.

Primary Examiner—Mukund J. Shah
Assistant Examiner—Michael Bucknum
Attorney, Agent, or Firm—Hale and Dorr LLP

[57] ABSTRACT

This invention is directed to nitric esters of derivatives of propionic acid, 1-(p-chlorobenzoyl)-5-methoxy-2-methyl-3-indolylacetic acid, 5-benzoyl-1,2-dihydro-3H-pyrrolo[1,2-a]pyrrole-1-carboxylic acid, 6-methoxy-2-napthylacetic acid, characterized in that they have the following general formula:

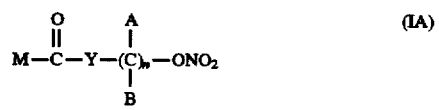

(IA)

These nitric ester derivatives may be formulated into pharmaceutical compositions and administered for their anti-inflammatory and/or analgesic activity.

13 Claims, No Drawings

NITRIC ESTERS HAVING ANTI-INFLAMMATORY AND/OR ANALGESIC ACTIVITY AND PROCESS FOR THEIR PREPARATION

OBJECT OF THE INVENTION

This application is a 371 of PCT/EP94/03182 dated Sep. 23, 1994.

The present invention refers to nitric esters of derivatives of propionic acid, 1-(p-chlorobenzoyl)-5-methoxy-2-methyl-3-indolylacetic acid, 5-benzoyl-1,2-dihidro-3H-pyrrolo[1,2-a]pyrrole-1-carboxylic acid, 6-methoxy-2-naphthylacetic acid, their pharmaceutical utilization and the process for their preparation. The present invention also refers to pharmaceutical compositions comprising at least one of said nitric esters as active constituent.

PRIOR ART

Some derivatives of propionic acid, such as, for instance, 2-(6-methoxy-2-naphtyl)propionic acid 2-(4-isobutylphenyl) propionic acid or alpha-Methyl-4-[(2-oxocyclopentyl)methyl]benzeneacetic acid, have been used for a long time in the pharmaceutical field for their anti-inflammatory activity and have been present for many years on the different world markets. The process for the preparation of 2-(6-methoxy-2-naphtyl)propionic acid has been described in the South African Patent No. 6707,597, in the German Patent No 1,934,460, corresponding to the U.S. Pat. No. 3,637,767 and also in C.A. 71, 91162j (1969); HARRISON et al. J. Med. Chem. 13,203 (1970); the process for the preparation of 2-(4-isobutylphenyl) propionic acid has been described in Patents GB No 971,700, U.S. Pat. No. 3,228,831 and U.S. Pat. No. 3,385,886, and also in T. SHIORI, N. KAWAI, J. Org. Chem. 43,2936 (1978); J. T. PINHEY, B. A. ROWE, Tetrahedron Letters 21, 965 (1980) while the process for the preparation of alpha-methyl-4-[(2-oxocyclopentyl)methyl]benzenacetic acid has been described in the German Patent No. 2,814,556 and in U.S. Pat. No. 4,161,538.

In the case of 2-(6-methoxy-2-naphtyl)propionic acid, the pharmacological profile is described in ROSZKOWSKI et el. J. Pharmacol. Exp. Ther. 179,114 (1971), while the pharmacological profile of 2-(4-isobutylphenyl)propionic acid is reported in ADAMS et al. Arch. Pharmacodyn. Ther. 178,115 (1969).

The utilization of these derivatives of propionic acid as anti-inflammatory agents involves, as known, extremely severe adverse reactions affecting, for instance, the gastrointestinal system, as well as damages to liver and kidneys.

Other particularly toxic products are, for example, 5-benzoyl-,2-dihydro-3H-pyrrolo[1,2-a]pyrrole 1-carboxylic acid or Ketorolac [W. H. ROOKS et el. Agents Actions 12,684 (1982)] and 1-(4-chlorobenzoyl)-5-methoxy-2-methyl-1H-indole-3-acetic acid or Indomethacin [C. D. KLAASSEN, Toxicol. Appl. Pharmacol. 28,127 (1976)]. in particular, in some countries Ketorolac has been withdrawn from the market because of its gastrointestinal toxicity, while Indomethacin is one of the drugs which has caused the highest death-rate from the year of its introduction in the market. Compared with other known anti-inflammatory and/or analgesic drugs, Ketorolac and Indomethacin cause—because of the already described adverse reactions—very extensive damages and, in particular as concerns gastrointestinal toxicity, deaths have been ascertained even in children.

It is therefore evident that there is the need of having drugs which, though providing a good anti-inflammatory and/or analgesic activity, do not result to be, in general, toxic.

OBJECTS OF THE INVENTION

Object of the present invention is that of providing a product which, while assuring at least the maintenance of the pharmacological activity which is characteristic of the known anti-inflammatory and/or analgesic agents, is capable of eliminating the adverse reactions brought about by the treatment with said agents, and has good tolerance.

Another object of the present invention is that of realizing a process for the preparation of derivatives of propionic acid, 1-(p-chlorobenzoyl)-5-methoxy-2-methyl-3-indolylacetic acid, 5-benzoyl -1,2-dihidro-3H-pyrrolo[1,2-a]pyrrole-1-carboxylic acid, 6-methoxy-2-naphthylacetic acid, having an anti-inflammatory and/or analgesic activity, good tolerance and being exempt from the adverse reactions that are typical of anti-inflammatory and analgesic agents.

Still another object of the present invention is that of providing pharmaceutical compositions having anti-inflammatory and/or analgesic activity which results provided with good tolerance.

DESCRIPTION OF THE INVENTION

These and still further objects and associated advantages which shall clearly result from the following description, are reached by derivatives of propionic acid, 1-(p-chlorobenzoyl)-5-methoxy-2-methyl -3-indolylacetic acid, 5-benzoyl -1,2-dihidro -3H-pyrrolo[1,2-a]pyrrole-1-carboxylic acid, 6-methoxy-2-naphthylacetic acid which, according to the present invention, have the following general formula:

$$M-\overset{O}{\underset{}{C}}-Y-\underset{\underset{B}{|}}{\overset{\overset{A}{|}}{C}}_n-ONO_2 \quad (IA)$$

where:

A and B are chosen among hydrogen, linear or branched, substituted or non substituted alkyl chains, M is chosen among:

 (XXX)

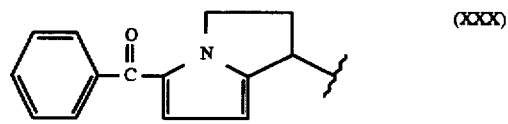 (XXXI)

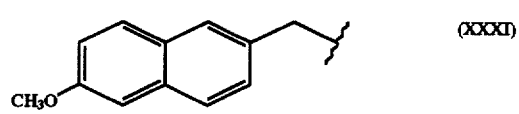

 (XXXII)

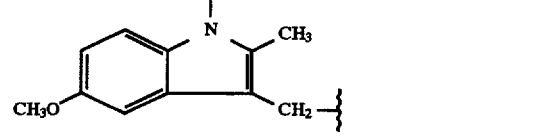

 (XXXIII)

where R is chosen among:

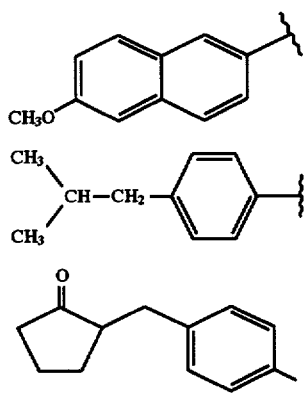

Y is chosen among oxygen, NH, NR$_1$, where R$_1$ is a linear or branched alkyl group, and n is comprised between 1 and 10.

More particularly, the fragment

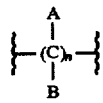

is a linear, branched or cyclic alkylenic group C$_2$–C$_{10}$. In fact, it has been observed that the introduction of a group such as a terminal nitric ester in the derivatives (IA) permits to mantain the pharmacological activity which is characteristic of anti-inflammatory non steroidal and/or analgesic agents, leads to products provided with good tolerance, while eliminating the adverse reactions caused by the treatment with such drugs. Furthermore, the introduction of a terminal nitric ester in the derivatives of propionic acid, permits to potentiate the anti-inflammatory effect compared with the well known non-steroidal anti-inflammatory drugs; such increase is made by the terminal nitric ester group, which can be considered as a source of nitric oxide and which can exert additional anti-inflammatory effects.

It has been also observed that the derivatives (IA) are useful in the treatment of different unhealthy conditions, for instance unhealthy conditions which required the treatment with both anti-inflammatory and analgesic drug, or rheumatic diseases in general, disorders of an immunologic nature, and they can also alleviate moderate-medium painful states of any kind.

Moreover, the derivatives (IA) subject matter of this invention, are useful in the treatment of the illnesses of the cardiovascular system and of the central nervous system, in particular in the treatment of myocardial and brain ischemiae, as well as in some cases of arterial thrombosis and in some cases of senile dementia. Always according to this invention, a nitric ester (IA) proved to be particularly advantageous, where: hydrogen is chosen as A and B, M is chosen as

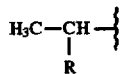

(XXXIII)

where R is chosen as:

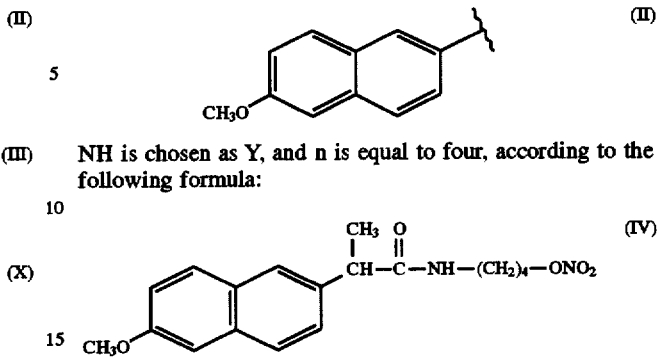

NH is chosen as Y, and n is equal to four, according to the following formula:

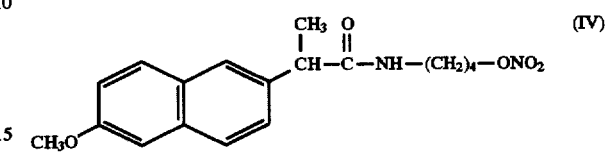

A nitric ester (IA) has also proved to be particularly advantageous according to this invention, where: hydrogen is chosen as A and B, M is chosen as

(XXXIII)

where R is chosen as:

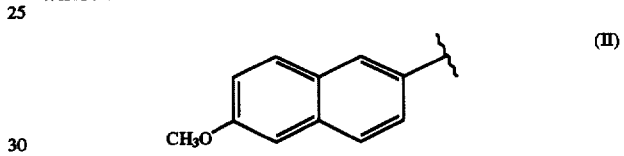

oxygen is chosen as Y, an n is equal to four, according to the following formula:

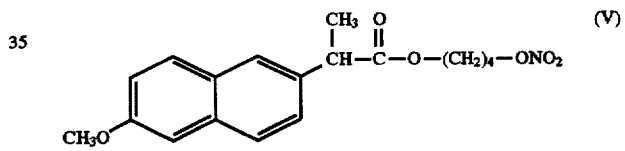

Also the nitric esters of derivatives of 2-(4-isobutylphenyl)propionic acid have proved to be particularly advantageous according to this invention, having the following formulae:

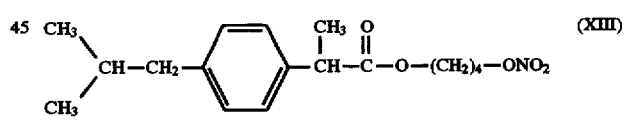

and

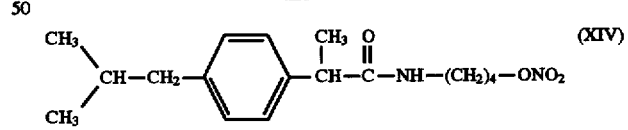

Always according to the present invention, nitric esters (IA) have proved to be particularly advantageous, having the following formulae:

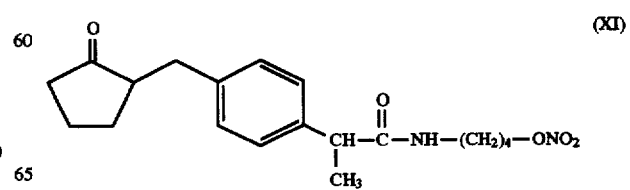

-continued

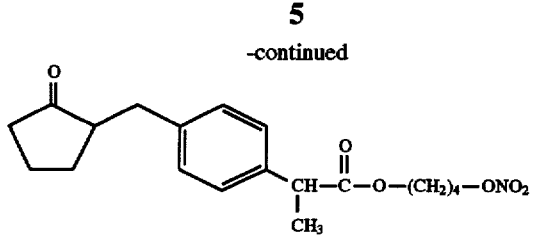
(XII)

Always according to the present invention, nitric esters (IA) where M is chosen as

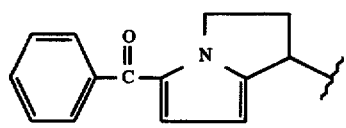
(XXX)

oxygen is chosen as Y, hydrogen is chosen as A and B and n is equal to four according to the following formula:

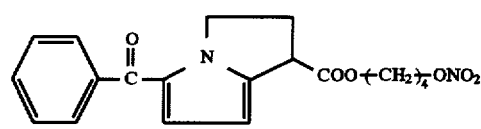
(XXXIV)

proved to have very good tolerance.

For the preparation of nitric esters (IA) subject matter of the present invention, a first process has proved to be particularly advantageous which, according to the present invention, includes the following steps:

Preparation of sodium salt of derivatives having the following general formula:

(VIA)

where M is chosen among (XXX), (XXXI), (XXXII),

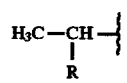
(XXXIII)

where R is chosen among the following structures:

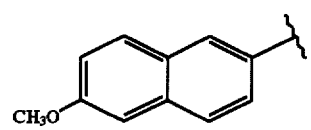
(II)

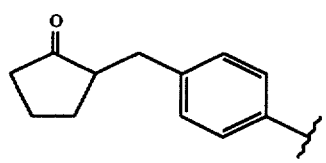
(X)

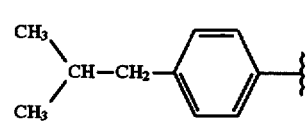
(III)

or preparation of derivatives (VIA) functionalized to the carboxylic group as acylic chlorides, anhydrides or the like;

Reaction between the sodium salt of said derivatives (VIA) or of said derivatives (VIA) functionalized to the carboxylic group, with a composition having the following general formula:

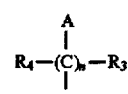
(VII)

where:

$R_4$ is chosen among chlorine, bromine, $NHR_5$ with $R_5$ hydrogen, linear or branched alkyl chain, A and B are chosen among hydrogen, linear or branched, substituted or non substitutes alkyl chains, $R_3$ is chosen among chlorine, bromine and iodine, and n is comprised between 1 and 10, with ensuing production of the relevant monomeric esters or the relevant amides;

Reaction of said monomeric esters or said amides with a nitrating agent such as $AgNO_3$ or the like, with ensuing production of nitric esters (IA).

A second process has also proved to be particularly advantageous which, always according to the present invention, includes the following steps:

Preparation of sodium salt of derivatives having the following general formula:

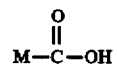
(VIA)

where M is chosen among (XXX), (XXXI), (XXXII), (XXXII)

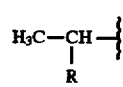
(XXXIII)

where R is chosen among the following structures:

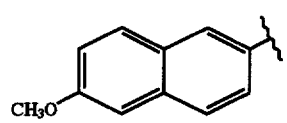
(II)

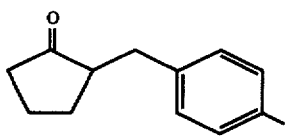
(X)

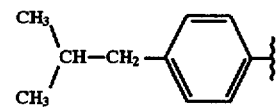
(III)

or preparation of derivatives (VIA) functionalized to the carboxylic group, such as acylic chlorides, anhydrides or the like;

Reaction between the sodium salt of said derivatives (VIA) or of said derivatives (VIA) functionalized to the carboxylic group, with a composition having the following general formula:

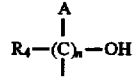
(VIII)

where;

$R_4$ is chosen among chlorine, bromine, $NHR_5$ with $R_5$ hydrogen, linear or branched alkyl chains, A and B are chosen among hydrogen, linear or branched, substituted or non substituted alkyl chains, and n is comprised between 1 and 10, with ensuing production of the relevant monomeric esters or the relevant amides;

Reaction of said monomeric esters or said amides with an halogenating composition such as PBr₃ or the like, with ensuing production of said monomeric esters or said amides characterized by the presence of a terminal halogen group;

Reaction of said monomeric esters or said amides characterized by the presence of a terminal halogen group, with a nitrating agent such as AgNO₃ or the like, with ensuing production of nitric esters of derivatives (IA).

The solvents which are utilized in the processes subject matter of the present invention are preferably chosen among chloroform, methylene chloride, acetonitrile, dimethylformamide, tetrahydrofuran, 1,4-dioxane and the like.

Such processes for the preparation of derivatives (IA), subject matter of the present invention, consist of a limited number of steps, which permits to obtain in a short time the products which derive from these processes, with satisfactory yields and in high amounts, also on the industrial level.

According to the processes subject matter of this invention, the preparation of a nitric ester derived from propionic acid has proved to be particularly advantageous, having the following formula:

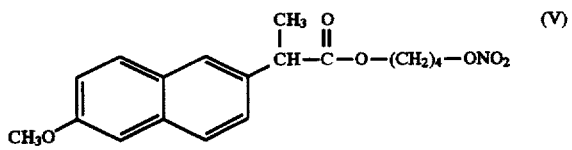

which is prepared as described in the example that is given hereunder as a mere indication and which does not limit in any way the protection scope of the invention.

EXAMPLE 1 a) 0.59 g of EtONa dissolved in 10 ml of ethyl alcohol were added, by slow dripping, to a solution of 2 g of 2-(6-methoxy-2-naphtyl)propionic acid, dissolved in 20 ml of ethyl alcohol. The reaction mixture was stirred for 5 minutes at room temperature, then the solvent was evaporated at a reduced pressure, obtaining 2.1 g of sodium salt of 2-(6-methoxy-2-naphtyl)propionic acid. The 2.1 g of sodium salt of 2-(6-methoxy-2-naphtyl) propionic acid so obtained were disperded in 40 ml of dimethylformamide and 1.5 g of 1-Br-4-Cl-butane dissolved in 30 ml of dimethylformamide were added by dripping to this dispersion. The reaction mixture was stirred for 12 hours at room temperature, then diluted with water and extracted with methylene chloride. The organic phase so extracted was anhydrified on sodium sulfate and the solvent was evaporated at a reduced pressure until a dry residue of 2 g was obtained. The residue was purified by chromatography on silica gel, utilizing an eluting mixture constituted by hexane/ether 7/3 (v/v).

The head fractions were collected, the solvent was evaporated at a reduced pressure and 1 g of 2-(6-methoxy-2-naphtyl) propionate of 4-chlorobutyl (IX) was obtained.

IR(cm⁻¹): C=0,1669.

¹H-NMR(300 MHz) (CDCl₃): 1.6 ppm (d,3H); 1.75 ppm (m, 4H); 3.45 ppm (m, 2H); 3.88 ppm (g, 1H); 3.91 ppm (1,3H); 4.1 ppm (m, 2H); 7.1–7–7.7 ppm (m, aromatics).

Mass spectrometry (i.e.): M⁺320.

b) 0.79 g of AgNO₃ dissolved in 1.3 ml of acetonitrile were dripped to 1 g of (IX) obtained as described in a), dissolved in 4,5 ml of acetonitrile. The reaction mixture was stirred for 12 hours at a temperature of 85° C. and then filtered.

From the resulting solution, the solvent was evaporated at a reduced pressure, and a residue was obtained to which 10 ml of methylene chloride were added. The mix so obtained was filtered once again, the organic phase was washed with water and then anhydrified on sodium sulfate. The solvent was evaporated under reduced pressure and 1.8 g of a dry residue was obtained, which was purified by chromatography on silica gel, utilizing an eluting mixture constituted by hexane/ether 7/3 (v/v). The fractions containing the product were collected, the solvent was evaporated at a reduced pressure and 1.5 g of nitric ester of 2-(6-methoxy-2-naphtyl) propionate of 4-hydroxy-butyl (V) were obtained.

IR(cm⁻¹): C=0,1733; ONO₂, 1637.

¹H-NMR(300 MHz) (CDCL₃): 1.6 ppm (d,3H); 1.65 ppm (m, 4H); 3.8 ppm (q, 1H); 3.9 ppm (s,3H); 4.1 ppm (m, 2H); 4.3 ppm (m, 2H); 7.1–7.7 ppm (m, aromatics).

Mass spectometry (i.e.) M⁺347.

Always according to the processes subject matter of the present invention, also the preparation of a nitric ester derivated from propionic acid proved to be particularly advantageous, having the following formula:

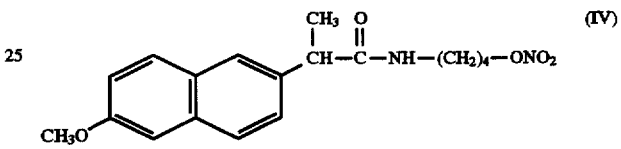

which is prepared as described in the following example, that is given hereunder as a mere indication and which does not limit in any way the protection scope of this invention.

EXAMPLE 2 a) 23.9 g of potassium-phtalimide dispersed into 200 ml of anhydrous dimethylformamide were added to a solution of 55.7 g of 1,4-di bromo-butane dissolved in 300 ml of anhydrous dimethylformamide.

The reaction mixture was agitated for 12 hours at room temperature, then diluted with water and extracted with methylene chloride. The methylene chloride was evaporated from the organic phase so obtained at a reduced pressure and then the dimethylformamide was removed by distillation at the pressure of 10 mm Hg.

The residue was regained with water and extracted with methylene chloride.

Tha organic phase so obtained was anhydrified and the solvent was evaporated at a reduced pressure until 14.8 g of 1-phtalimide-4-bromo-butane were obtained, which were treated with isopropyl ether and then essiccated.

m.p.=77° C.

b) 32 ml of hydriodic acid were cautiously added to 8.25 g of 1-phtalimido-4-bromo-butane; the mixture was then submitted to heating and kept in ebullition for 24 hours.

After cooling, the mixture was diluted with water and after filtration the solvent was evaporated at a reduced pressure, obtaining a residue which, once crystallized by ethyl ether, produced 6 g of 4-iodine-butylammonium iodide.

m.p.=103° C.

c) 7 ml of thionyl chloride were cautiously added to a solution of 2.3 g of 2-(6-methoxy-2-naphtyl)propionic acid in 15 ml of anhydrous chloroform. The reaction mixture was stirred for 40 minutes at room temperature and then the solvent was evaporated at a reduced pressure, obtaining 2.23 g of 2-(6-methoxy-2-naphtyl)propionylchloride.

2.3 g od 2-(6-methoxy-2-naphtyl)propionylchloride were dissolved in pyridine and the solution was cooled at the temperature of 0° C.

3.27 g of 4-iodobutylammonium iodide were added to this solution and the mixture so obtained was agitated for 1 hour at 0° C. and then diluted with water and extracted with methylene chloride.

The organic phase so obtained was washed initially with a 10% solution of hydrochloric acid and afterward with a saturated solution of sodium bicarbonate, then the solvent was evaporated at a reduced pressure, obtaining 3.2 g of a dry residue. The residue was purified by chromatography on silica gel, utilizing methylene chloride as eluent.

The intermediate fractions were collected, the solvent was evaporated at a reduced pressure and 1.6 g of 2-(6-methoxy-2-naphtyl)-4-iodobutyl propionamide (XX) were obtained.

IR (cm$^{-1}$): NH, 3294; C=0,1651.

$^1$H-NMR (300 MHZ) (CDCl$_3$): 1.1–1.75 ppm (m, 4H); 1.6 ppm (d, 3H); 3.1 ppm (t, 2H); 3.2 ppm (q, 2H); 3.7 ppm (q, 1H); 3.9 ppm (s, 3H); 5.35 ppm (m, NH); 7.1–7.75 ppm (m, aromatics).

d) A suspension of 1.6 g of 2-(6-methoxy-2-naphtyl)-4-iodobutyl propionamide in 20 ml of acetonitrile was heated at a temperature of about 40° C. and stirred until a solution was obtained to which 1.0 g of AgNO$_3$ were added.

The mixture was stirred for 1 hour at room temperature, then filtered and the solvent was evaporated at a reduced pressure. The residue obtained was regained with methylene choride, the resulting mixture was filtered and the solvent was evaporated at a reduced pressure, and 0,8 g of dry residue were obtained which were purified by chromatography on silica gel, utilizing an eluting mixture constituted by methylene chloride/ethyl acetate 9/1 (v/v).

The head fractions were collected, the solvent was evaporated at a reduced pressure and 0.75 g of nitric ester of 2-(6-methoxy-2-naphtyl)-4-hydroxybutyl propionamide (IV) were obtained.

IR(cm$^{-1}$): C=0,1672; NH, 3294; ONO$_2$, 1637

Mass spectometry (i.e.) M$^+$346.

$^1$H-NMR (80 mhz) (CDCl$_3$): 1.3 ppm–1.6 ppm (m, 4H); 1.7 ppm (d, 3H); 3.1 ppm (q, 2H); 3.7 ppm (q, 1H); 3.9 ppm (s, 3H); 4.3 ppm (m, 2H); 5.6 ppm (m, NH); 7.05–7.8 ppm (m, aromatics).

Always according to the present invention, also the nitric ester having the following formula:

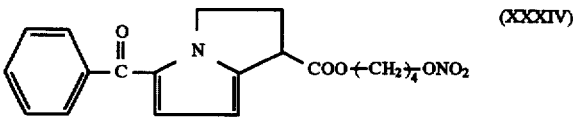
(XXXIV)

proved to be particularly advantageous, which is prepared as described in the following example that is also given hereunder as a mere indication and which does not limit in any way the protection scope of this invention.

EXAMPLE 3

Preparation of the composition having the formula:

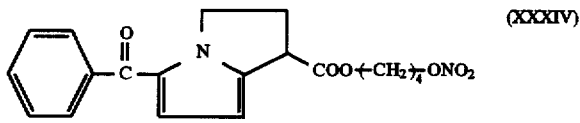
(XXXIV)

a) In a suspension of 80% sodium hydride (0,16 g) in DMF (15 ml), 1,5 g of Ketorolac dissolved in 20 ml of DMF were caused to drip under agitation.

The reaction mix was kept under agitation at 40° C. for 15 minutes, then 1 ml of 1,4-dibromobutane was added and the mix was kept under agitation at room temperature overnight.

Then the solvent was evaporated under reduced pressure and the residue was treated with water and methylene chloride. The organic phase was separated, dryed on sodium sulfate and the solvent was removed under reduced pressure, to obtain a residue which was purified by silica gel chromatography, utilizing a 4/6 petroleum ether/ether eluent mix (v/v). The head fractions were collected, the solvent was evaporated under reduced pressure and 0.75 g of product was obtained having the formula:

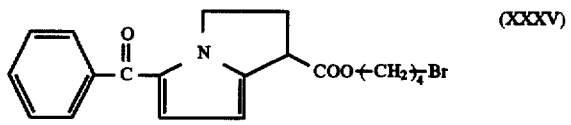
(XXXV)

$^1$H-NMR (80 MHz) (CDCl$_3$) (ppm): 1,83(6H, m); 2,81 (2H, m); 3,38(2H, t); 4,12(2H, t); 4,48(1H,m); 6,03(1H, d); 6,78(1H,d); 7,41(3H, m); 7,73(2H, m).

b) A solution of AgNO$_3$ (0,5 g) in 5 ml of acetonitrile was added to a solution of (XXXV) (0,75 g) in 20 ml of acetonitrile. The reaction mix was kept stirring at room temperature for 48 hours. The solvent was then removed under pressure and the residue was treated with water and methylene chloride. The organic phase was then separated, dryed on sodium sulfate and the solvent was removed under reduced pressure. The residue was purified by filtration on silica gel, utilizing a 4/6 petroleum ether/ether eluent mix. The head fractions were collected, the solvent was evaporated under reduced pressure and 0.35 g of (XXXIV) were obtained. $^1$H-NMR (80 MHz) (CDCl$_3$)(ppm): 1.78(6H, m); 2.82(2H, m); 4.14(2H, m); 4.47(3H, m); 6.02(1H, d); 6.79 (1H, d); 7.46(3H, m); 7.77(2H, m).

Through biological assays the anti-inflammatory and analgesic activity were determined, for instance of nitric esters (IA) having the following formulae:

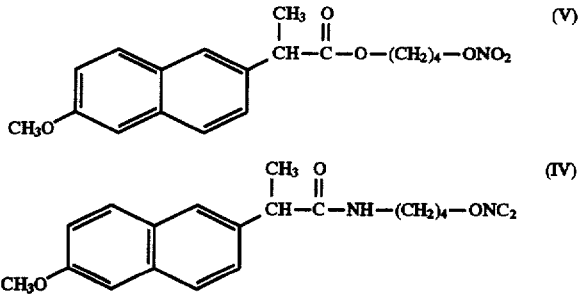

The anti-inflammatory activity of said nitric esters of derivatives of propionic acid was determined in Wistar rats utilizing the method of carrageenan edema, as reported in C. A. WINTER, E. RISLEY, G. W. NUSS, Proc. Soc. Exp.

Biol. Med. 111,544–547 (1962), while the analgesic activity of said derivatives was determined in Swiss mice as reported by L. C. HENDERSHOT, J. FORSAITH, J. Pharmacol. Exp. Ter. 125,237–249 (1959).

The anti-inflammatory and analgesic activity of said derivatives resulted to be comparable to 2-(6-methoxy-2-naphtyl)propionic acid taken as a reference.

The anti-platelet aggregation activity of said derivatives was determined on human platelets. Platelets were incubated with the compounds for 10 min at 37° C. prior to stimulation with trombin. The anti-platelet aggregation activity of said derivatives resulted to be comparable to 2-(6-methoxy-2-naphthyl)propionic acid taken as a reference.

Then, the acute toxicity of said derivatives (IV) and (V) was evaluated by oral administration of a single dose of each composition (IV) and (V), utilizing groups of 10 Swiss mice for each derivative.

The incidence of lethality and the onset of a toxic symptomatology were reported for an observation period of 14 days.

Even after the administration of a dose of 750 mg/kg of composition (IV) or composition (V) no apparent toxicity simptoms were observed in the treated animals. Further biological assays were carried out in order to define the pharmaco-toxicological profile of the studied compounds, in particular of composition (V), compared with 2-(6-methoxy-2-naphtyl)propionic acid taken as reference.

A. PHARMACODYNAMIC ACTIVITY

Acute Models

Rat carrageenan paw edema. On the basis of preliminary experiments, the compound (V) and 2-(6-methoxy-2-naphtyl)propionic acid prove to have a comparable efficacy; the effective dose is comprised in the range from 1 to 10 mg/kg p.o.

Subacute Models

Rat adjuvant arthritis. The animals treated for 19 running days (from the 3rd to the 20th day after the inducing injection) with composition (V) or with 2-(6-methoxy-2-naphtyl)propionic acid, both of them at doses of 3 mg/kg p.o., showed a significant and comparable reduction in arthritic symptomatology compared with controls.

B. GASTROINTESTINAL TOLERABILITY

Damage to the gastric mucosa of the rat. The compound (V) was studied in comparison with 2-(6-methoxy-2-naphtyl)propionic acid taken as reference, both of them at doses comprised between 3 and 30 mg/kg p.o.; the compound (V) proved to be significantly better tolerated than 2-(6-methoxy-2-naphtyl)propionic acid. 2-(6-methoxy-2-naphtyl)propionic acid already at 3 mg/kg caused gastric damages, and such effects resulted to be dose-dependent, while the compound (V) proved to be well tolerated even at doses of 30 mg/kg.

C. GENERAL PHARMACOLOGY

A secondary pharmacological evaluation of compound (V) was carried out in comparison with 2-(6-methoxy-2-naphtyl)propionic acid. No considerable additional effects with respect to the primary pharmacological activity were observed on central nervous system, on the autonomous system, on the cardiovascular, respiratory and gastrointestinal systems.

D. TOXICOLOGY

Acute toxicity in rodents. Preliminary studies were carried out in rodents, utilizing two administration routes. No simptoms of apparent toxicity were observed in animals treated with oral or intraperitoneal doses of 300 mg/kg.

Maximum tolerated dose in non-rodents. Preliminary studies have indicated that compound (V) was very well tolerated in the dog, an animal species which is known to be particularly sensitive to the ulcerogenic activity of anti-inflammatory agents in general. The animals received increasing oral doses of compound (V) up to 30 mg/kg and no apparent symptoms were observed. In comparison, 2-(6-methoxy-2-naphtyl)propionic acid, administered at doses of 10 mg/kg, caused the death of the animals.

Furthermore, biological studies concerning nitric esters (IA) having the following formulae:

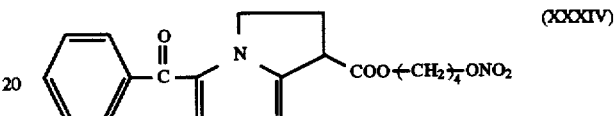

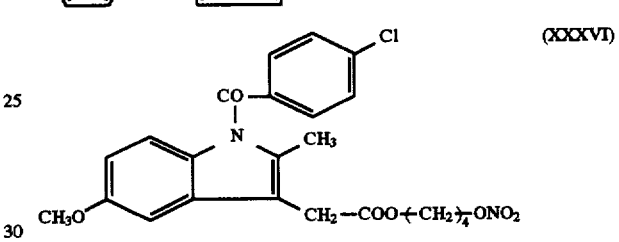

were carried out.

Then the anti-inflammatory activity, the gastrointestinal tolerability and the platelet anti-aggregating activity of the above compositions were determined.

The anti-inflammatory activity was determined by the method of the carrageenan edema in the rat, as described by C. A. WINTER et el. (1962) Proc. Soc. Exp. Biol. Med. 111,544. The gastrointestinal tolerability was evaluated by oral administration in the rat. The platelet anti-aggregating activity was determined on human platelets stimulated by arachidonic acid, according to the method described by V. BERTELE et el. (1983) Science 220, 517.

The results are shown on Table 1 as values concerning the anti-inflammatory, anti-aggregating activity and the gastrointestinal tolerability of the compositions under examination, expressed as a power ratio relatively to the basic product taken as a unity standard.

TABLE 1

| COMPOSITION | ANTI-INFLAMM. ACTIVITY | ANTI-AGGREG. ACTIVITY | GASTROINTEST. ULCEROGEN. |
|---|---|---|---|
| (XXXIV) | 1, 25 | 1, 10 | 0, 15 |
| KETOROLAC | 1, 0 | 1, 0 | 1, 0 |
| (XXXVI) | 1, 0 | 1, 30 | 0, 1 |
| INDOMETHACIN | 1, 0 | 1, 0 | 1, 0 |

The acute toxicity of the compositions under examination has been approximately evaluated by oral administration of a single dosage of the substance to groups of 10 mice. The death-rate incidence and the onset of toxic symptoms have been observed for a period of 14 days. Even after the administration of 100 mg/kg of each composition, the animals did not show any symptom of apparent toxicity.

What is claimed is:

1. Derivatives of propionic acid, 1-(p-chlorobenzoyl)-5-methoxy-2-methyl-3-indolylacetic acid, 5-benzoyl-1,2- dihidro-3H-pyrrolo[1,2-a]pyrrole-1-charboxylic acid, 6-methoxy-2-napthylacetic acid, characterized in that they have the following general formula:

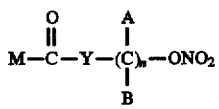 (IA)

where:

A and B are chosen from hydrogen, linear or brached, substituted or non substituted alkyl chains, M is chosen from:

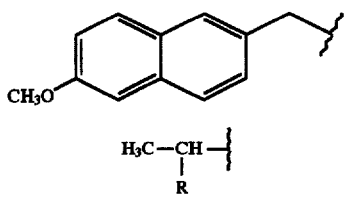 (XXXI)

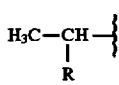 (XXXIII)

where R is chosen from:

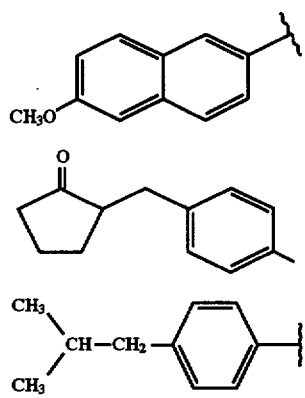

(II)

(X)

(III)

Y is chosen among oxygen, NH, NR$_1$, where R$_1$ is a linear or branched alkyl group, and n is an integer from 1 and 10.

2. Nitric esters according to claim 1, characterized in that the fragment:

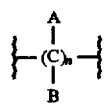

is a linear, branched or cyclic alkylenic group C$_2$-C$_{10}$.

3. Derivatives of propionic acid according to claim 1, characterized in that M is equal to

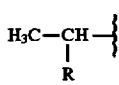 (XXXIII)

where R is:

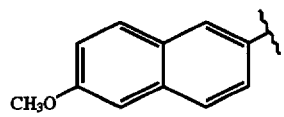 (II)

A and B are equal to hydrogen, Y is equal to oxygen, and n is equal to four.

4. Derivatives of propionic acid according to claim 1, characterized in that M is equal to

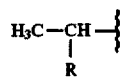 (XXXIII)

where R is:

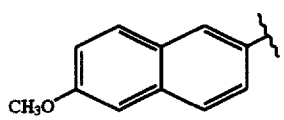 (II)

A and B are equal to hydrogen, Y is equal to NH, and n is equal to four.

5. Derivatives of propionic acid according to claim 1, characterized in that M is equal to

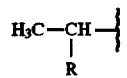 (XXXIII)

where R is equal to:

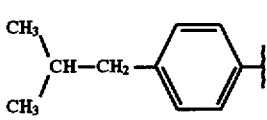 (III)

Y is equal to oxygen, A and B are equal to hydrogen, and n is equal to four.

6. Derivatives of propionic acid according to claim 1, characterized in that M is equal to

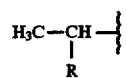 (XXXIII)

where R is equal to:

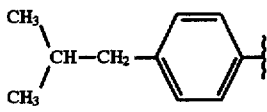 (III)

Y is equal to NH, A and B are equal to hydrogen, and n is equal to four.

7. Derivatives of propionic acid, according to claim 1, characterized in that M is equal to

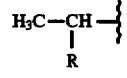 (XXXIII)

where R is equal to

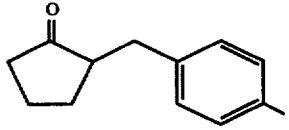 (X)

A and B are equal to hydrogen, y is equal to oxygen and n is equal to four.

8. Derivatives of propionic acid according to claim 1, characterized in that M is equal to

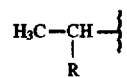 (XXXIII)

where R is equal to

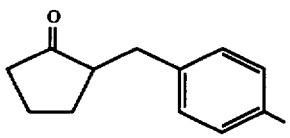 (X)

A and B are equal to hydrogen, y is equal to NH and n is equal to four.

9. A pharmaceutical composition comprising at least one nitric acid compound as claimed in claim 1 and a pharmaceutical acceptable carrier.

10. The pharmaceutical composition of claim 9, wherein said composition has anti-inflammatory activity.

11. The pharmaceutical composition of claim 9, wherein said composition has analgesic activity.

12. The pharmaceutical composition of claim 9, wherein said composition is used in the treatment of rheumatic diseases, immunological disorders, and moderate to medium painful conditions.

13. The composition of claim 9, wherein said composition is used in the treatment of diseases affecting the cardiovascular system, senile dementia, myocardial and brain ischemia, and arterial thrombosis.

* * * * *

(12) EX PARTE REEXAMINATION CERTIFICATE (5605th)
United States Patent
Del Soldato

(10) Number: US 5,700,947 C1
(45) Certificate Issued: Nov. 14, 2006

(54) NITRIC ESTERS HAVING ANTI-INFLAMMATORY AND/OR ANALGESIC ACTIVITY AND PROCESS FOR THEIR PREPARATION

(75) Inventor: Piero Del Soldato, Monza (IT)

(73) Assignee: NICOX S.A., Paris (FR)

Reexamination Request:
No. 90/007,599, Jun. 21, 2005

Reexamination Certificate for:
Patent No.: 5,700,947
Issued: Dec. 23, 1997
Appl. No.: 08/624,508
Filed: Apr. 5, 1996

(22) PCT Filed: Sep. 23, 1994

(86) PCT No.: PCT/EP94/03182

§ 371 (c)(1),
(2), (4) Date: Apr. 5, 1996

(87) PCT Pub. No.: WO95/09831

PCT Pub. Date: Apr. 13, 1995

(30) Foreign Application Priority Data

Oct. 6, 1993 (GB) .............................................. 9320599
May 10, 1994 (IT) ......................................... MI94A0916

(51) Int. Cl.
*C07C 203/04* (2006.01)
*C07C 203/00* (2006.01)
*C07D 209/28* (2006.01)
*C07D 209/00* (2006.01)
*C07D 487/04* (2006.01)

(52) U.S. Cl. ....................... 548/491; 548/576; 558/482; 558/483; 514/509

(58) Field of Classification Search ....................... None
See application file for complete search history.

(56) References Cited

FOREIGN PATENT DOCUMENTS

JP 54-081222 6/1979

*Primary Examiner*—Evelyn Mei Huang

(57) ABSTRACT

This invention is directed to nitric esters of derivatives of propionic acid, 1-(p-chlorobenzoyl)-5-methoxy-2-methyl-3-indolylacetic acid, 5-benzoyl-1,2-dihydro-3H-pyrrolo[1,2-a]pyrrole-1-carboxylic acid, 6-methoxy-2-napthylacetic acid, characterized in that they have the following general formula:

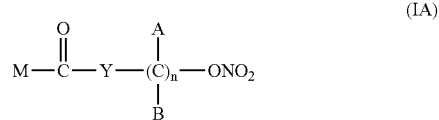

(IA)

These nitric ester derivatives may be formulated into pharmaceutical compositions and administered for their anti-inflammatory and/or analgesic activity.

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

AS A RESULT OF REEXAMINATION, IT HAS BEEN DETERMINED THAT:

The patentability of claims 3–8 is confirmed.

Claim 1 is determined to be patentable as amended.

Claims 2 and 9–13, dependent on an amended claim, are determined to be patentable.

New claims 14, 15 and 16 are added and determined to be patentable.

1. Derivatives of propionic acid, 1-(p-chlorobenzoyl)-5-methoxy-2-methyl-3-indolylacetic acid, [5-benzoyl-1,2-dihidro-3H-pyrrolo[1,2-a]pyrrole-1-charboxylic] *5-benzoyl-1,2-dihydro-3H-pyrrolo[1,2-a]pyrrole-1-carboxylic* acid, *and* 6-methoxy-2-napthylacetic acid, characterized in that they have the following general formula:

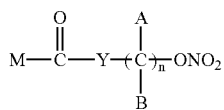

(IA)

where:
A and B are chosen from hydrogen, *and* linear [or brached] *branched*, substituted [or], *and* non substituted alkyl chains, M is chosen from:

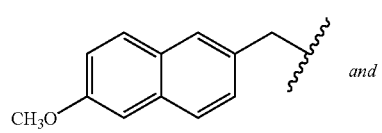

(XXXI)

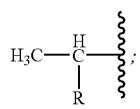

(XXXIII)

where R is chosen from:

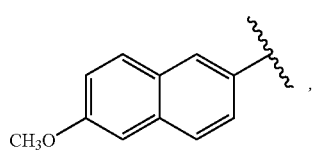

(II)

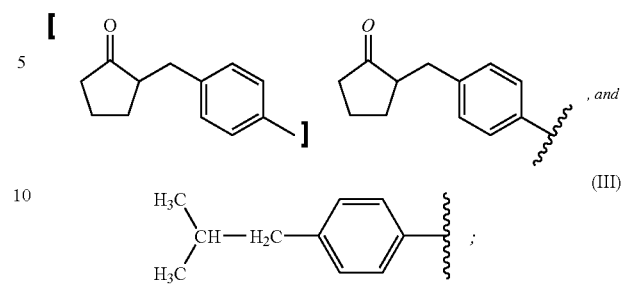

(X)

[ ] (III)

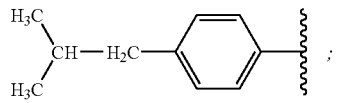

Y is chosen [among] *from* oxygen[,] *and* NH[, NR$_1$, where R$_1$ is a linear or branched alkyl group], and n is an integer from 1 [and] *to* 10;

*provided that n is 4 when A is hydrogen, B is hydrogen, M is formula (XXXIII), R is formula (III), and Y is NH.*

*14. Derivatives of propionic acid, 1-(p-chlorobenzoyl)-5-methoxy-2-methyl-3-indolylacetic acid, 5-benzoyl-1,2-dihydro-3H-pyrrolo[1,2-a]pyrrole-1-carboxylic acid, and 6-methoxy-2-napthylacetic acid, having the following general formula:*

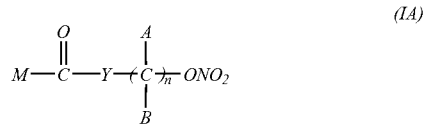

(IA)

*wherein:*
*A and B are selected from hydrogen, and linear, branched, substituted, and non-substituted alkyl chains;*
*M is selected from:*

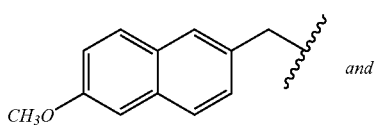

(XXXI)

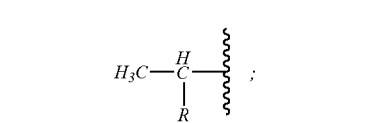

(XXXIII)

*wherein R is selected from:*

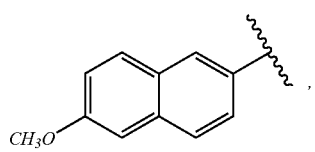

(II)

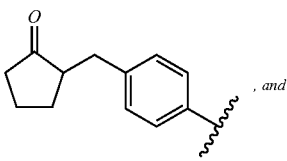

(X)

-continued

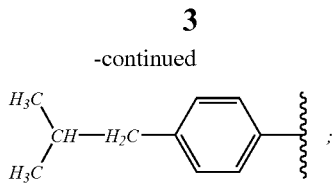
(III)

Y is selected from oxygen, NH, and $NR_1$, wherein $R_1$ is a linear or branched alkyl group; and n is an integer from 4 to 10.

15. Derivatives of propionic acid, 1-(p-chlorobenzoyl)-5-methoxy-2-methyl-3-indolylacetic acid, 5-benzoyl-1,2-dihydro-3H-pyrrolo[1,2-a]pyrrole-1-carboxylic acid, and 6-methoxy-2-napthylacetic acid, having the following general formula:

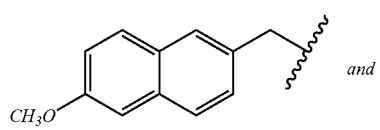
(IA)

wherein:

A and B are selected from hydrogen, and linear, branched, substituted, and non-substituted alkyl chains;

M is selected from:

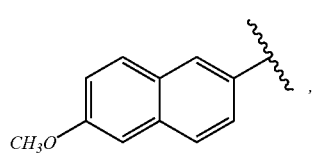
and
(XXXI)

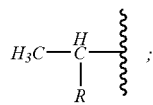
(XXXIII)

wherein R is selected from:

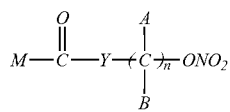
,
(II)

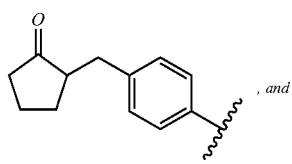
, and
(X)

-continued

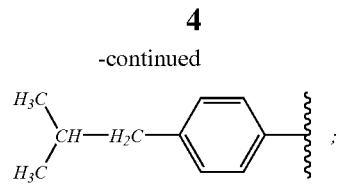
(III)

Y is oxygen; and n is an integer from 1 to 10.

16. Derivatives of propionic acid, 1-(p-chlorobenzoyl)-5-methoxy-2-methyl-3-indolylacetic acid, 5-benzoyl-1,2-dihydro-3H-pyrrolo[1,2-a]pyrrole-1-carboxylic acid, and 6-methoxy-2-napthylacetic acid, having the following general formula:

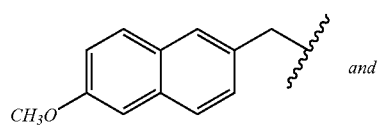
(IA)

wherein:

A and B are selected from hydrogen, and linear, branched, substituted, and non-substituted alkyl chains;

M is selected from:

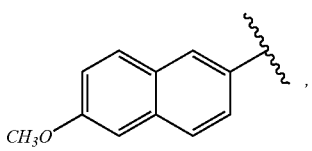
and
(XXXI)

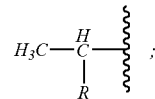
(XXXIII)

wherein R is selected from:

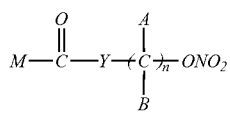
,
(II)

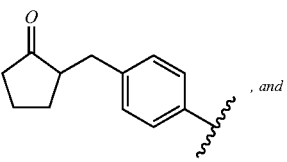
, and
(X)

Y is selected from oxygen, NH, and $NR_1$, wherein $R_1$ is a linear or branched alkyl group; and n is an integer from 1 to 10.

* * * * *